(12) United States Patent
Mills et al.

(10) Patent No.: US 7,053,251 B2
(45) Date of Patent: *May 30, 2006

(54) BROMINATION OF HYDROXYAROMATIC COMPOUNDS

(75) Inventors: Ryan Christopher Mills, Mechanicville, NY (US); John Yaw Ofori, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 238 days.

This patent is subject to a terminal disclaimer.

(21) Appl. No.: 10/650,566

(22) Filed: Aug. 28, 2003

(65) Prior Publication Data

US 2005/0049440 A1    Mar. 3, 2005

(51) Int. Cl.
*C07L 39/24* (2006.01)
(52) U.S. Cl. ..................................... 568/779
(58) Field of Classification Search ................. 568/779
See application file for complete search history.

(56) References Cited

U.S. PATENT DOCUMENTS

| | | | | |
|---|---|---|---|---|
| 3,987,068 | A | * | 10/1976 | Reilly ........................ 552/296 |
| 6,815,565 | B1 | * | 11/2004 | Mills et al. ................. 568/779 |
| 2004/0143144 | A1 | * | 7/2004 | Pressman et al. ........... 568/812 |

OTHER PUBLICATIONS

N. Narender et al., "Liquid phase bromination of phenols using potassium bromide and hydrogen peroxide over zeolites"; *Molec. Catalysis A: Chem.* 192, 73-77 (2003).

U.S. Appl. No. 10/342,475, filed Jan. 16, 2003, "Bromination of Hydroxyaromatic Compounds and Further Conversion to Dihydroxyaromatic Compounds".

K-J Lee et al., "Bromination of Activated Arenes by Oxone® and Sodium Bromide", *Bull. Korean Chem. Soc.* 22 (5), 773-74 (2002).

R. Neumann and I. Assael, "Oxybromination Catalysed by the Heteropolyanion Compound $H_5PMO_{10}V_2O_{40}$ in an Organic Medium: Selective para-Bromination of Phenol", *J. Chem. Soc., Chem. Commun.*, 1285-87 (1988).

U. Bora et al., "Regioselective Bromination of Organic Substrates by Tetrabutylammonium Bromide Promoted by $V_2O_5O_2$-$H_2O_2$: An Environmentally Favorable Synthetic Protocol", *Org. Lett.*, 2 (3), 247-49 (2000).

K. Krohn et al., "Para-Selective Chlorination and Bromination of Phenols with tert-Butyl Hydroperoxide and $TiX(OiPR)_3$", *J. Prakt. Chem.* 341 (1), 59-61 (1999).

T. Oberhauser, "A New Bromination Method for Phenols and Anisoles: $NBS/HBF_4$ $Et_2O$ In $CH_3CN$", *J. Org. Chem.* 62, 4504-06 (1997).

* cited by examiner

*Primary Examiner*—Michael L. Shippen
(74) *Attorney, Agent, or Firm*—Heslin Rothenberg Farley & Mesiti P.C.; Martha L. Boden

(57) ABSTRACT

A method for brominating hydroxyaromatic compounds to form products, such as p-bromophenol, is disclosed. The method uses elemental bromine as the brominating agent and comprises contacting a hydroxyaromatic compound with bromine and oxygen in the presence of metal catalyst. Suitable catalysts include elemental copper, copper compounds, and compounds of Group IV–VIII transition metals.

24 Claims, No Drawings

BROMINATION OF HYDROXYAROMATIC COMPOUNDS

CROSS-REFERENCE TO RELATED APPLICATIONS

This Application is related to the following U.S. patent applications/Patents:

This Application is related to the following U.S. patent applications: Ser. No. 10/342,475, filed Jan. 16, 2003, entitled "BROMINATION OF HYDROXYAROMATIC COMPOUNDS AND FURTHER CONVERSION TO DIHYDROXYAROMATIC COMPOUNDS", U.S. patent application Ser. No. 10/650,567, filed Aug. 28, 2003, entitled "SELECTIVE CATALYTIC OXYBROMINATION OF HYDROXYAROMATIC COMPOUNDS".

Each of these Applications is hereby incorporated by reference herein in its entirety.

BACKGROUND OF THE INVENTION

This invention relates to the catalyzed bromination of hydroxyaromatic compounds, and more particularly to the use of elemental bromine as the brominating agent in such reactions.

Monocyclic dihydroxyaromatic compounds such as hydroquinone and dihydroxybiphenyls such as 4,4'-dihydroxybiphenyl ("biphenol") have numerous uses in the chemical industry. For example, both compounds can be used in polymer preparation, notably in the preparation of polycarbonates, polysulfones and polyimides, especially polyetherimides.

There are various methods for the preparation of hydroquinone and biphenol. As examples of such methods, each compound can be prepared from p-bromophenol: hydroquinone by hydrolysis, and biphenol by reductive coupling in the presence of a noble metal catalyst, a base, and a reducing agent.

Brominated hydroxyaromatic compounds, as exemplified by p-bromophenol, are typically prepared by reaction of the precursor hydroxyaromatic compound with elemental bromine as the brominating agent in various solvents. However, this process is inefficient in its utilization of bromine because for every mole of bromoaromatic compound produced there is one mole of HBr generated, leading to only 50% conversion of elemental bromine to brominated products. Therefore, improved conversion of bromine to brominated products is desirable and has been pursued.

Several methods have been developed to increase the yield of brominated products with respect to elemental bromine. For example, hydrogen peroxide has been used in combination with the HBr produced during a typical bromination reaction. The use of peroxide facilitates the oxidation of HBr to $Br_2$ and therefore increases the yield of brominated products with respect to the initial amount of bromine charged to the reaction. Other methods include the use of a combination of various catalysts with a peroxide to facilitate the oxidation of HBr to bromine.

While these approaches provide additional efficiencies relative to other known methods, improved methods continue to be sought. In particular, it would be advantageous to conduct bromination reactions using elemental bromine as the brominating agent without producing HBr for several reasons. First, a higher percentage of valuable brominated products, such as p-bromophenol, can be obtained from a given amount of bromine. In addition, the ability to conduct such reactions without forming HBr allows for simplified downstream processing operations, such as eliminating the need for an HBr scrubbing unit and providing more flexibilty in material of construction for the majority of the downstream equipment.

SUMMARY OF THE INVENTION

The present invention provides a novel and efficient method for brominating hydroxyaromatic compounds using elemental bromine as the brominating agent, a metal catalyst, and an oxygen-containing gas. Unlike previous techniques, the present method unexpectedly provides for the transfer of both equivalents of Br from elemental bromine ($Br_2$) to the hydroxyaromatic substrate. The ability to do so is advantageous because it eliminates the formation of HBr and significantly increases the conversion of elemental bromine to brominated products, such as p-bromophenol.

Therefore, in one aspect, the present invention relates to a method for preparing a brominated hydroxyaromatic compound. The method comprises contacting a hydroxyaromatic compound with oxygen and elemental bromine in the presence of a metal catalyst.

In another aspect, the invention relates to a method for preparing 4-bromophenol, 4-bromo-2-methylphenol, or 4-bromo-3-methylphenol, which comprises contacting phenol, o-cresol or m-cresol with air and elemental bromine, in the presence of cupric bromide.

DETAILED DESCRIPTION OF THE INVENTION

The method of the present invention uses elemental bromine to brominate hydroxyaromatic compounds. Unexpectedly, however, the HBr produced from the bromination reaction is subsequently consumed by additional hydroxyaromatic compounds using oxygen in the presence of a metal catalyst. Unlike previous methods, the efficiency of $Br_2$ conversion to bromo-compounds exceeds 50%, and is usually greater than 70%, with efficiencies of 90% being observed. Thus, the present method allows for consumption of most of the bromine employed in the bromination reaction using inexpensive oxygen, such as in air, as an oxidant, and a metal catalyst.

The common initial reactant for all products obtained according to the method of this invention is a hydroxyaromatic compound, which may be an unsubstituted hydroxyaromatic compound such as phenol, or a substituted compound provided that the 4-position is unsubstituted and thus available for bromination. As one of skill would know, the 2-, 3-, and 4-positions relative to the carbon attached to the hydroxy group are also known as and referred to herein as ortho-, meta-, and para-, respectively. Furthermore, o-refers to ortho-; m-refers to meta-; and p-refers to para-. Note that a substituent may be located at any position of the aryl ring other than the 1- or 4-carbons. Exemplary substituents (one or more) are alkyl groups, particularly $C_{1-4}$ alkyl. Illustrative compounds are those having the formula

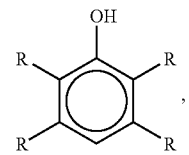

wherein each R is independently hydrogen or a substituent, preferably $C_{1-4}$ alkyl.

Particularly preferred in most instances is phenol, and specific reference will frequently be made to phenol hereinafter. However, homologous compounds such as o- and m-cresol may be substituted for phenol as desired.

The hydroxyaromatic compound is initially contacted with $Br_2$. For every mole of brominated compound produced, one mole of HBr is also produced, which, along with oxygen, contacts an additional hydroxyaromatic compound in the presence of a metal catalyst to form a second mole of the brominated compound. Each reaction may be conducted at a temperature ranging from about 20–150° C., but generally a temperature ranging from about 60–100° C. is preferred. The method of the present invention is illustrated by the following Scheme, using phenol as the hydroxyaromatic compound, and cupric bromide as the metal catalyst.

Scheme

Reaction (I): Consumption of First Br Equivalent

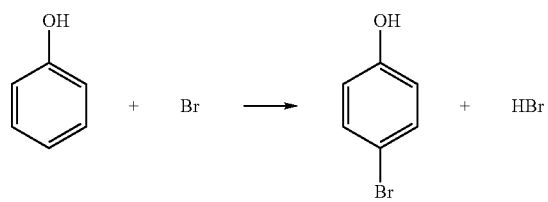

Reaction (II): Consumption of Second Br Equivalent

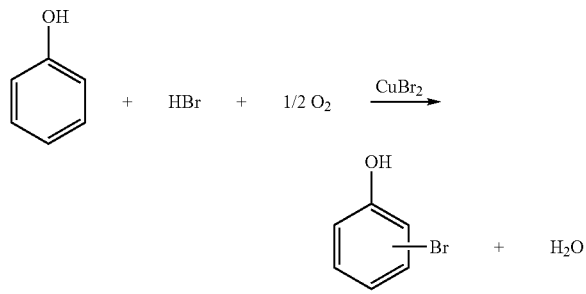

(III) Combined System: Reaction (I) + Reaction (II)

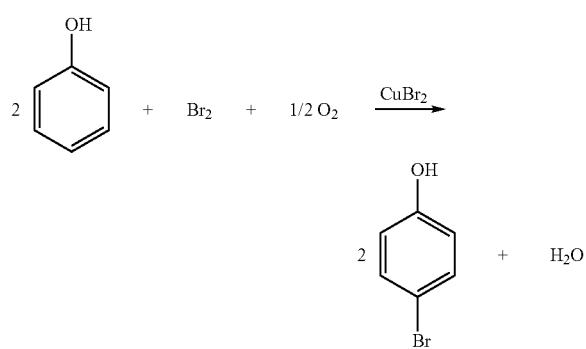

The above bromination reactions may be conducted sequentially by performing Reaction (I) first, followed by the addition of the metal catalyst to the reaction vessel and contacting the contents of the vessel with oxygen, as shown in Reaction (II). Alternatively, the metal catalyst can initially be added to the reactants of Reaction (I) (not shown) without the addition of oxygen. Then Reaction (II) is conducted by contacting the mixture from Reaction (I) with oxygen to consume the HBr produced therein. In another embodiment, all the ingredients may initially be combined in one vessel in the presence of oxygen, as depicted in the combined system (III).

In bromination Reaction (I), the hydroxyaromatic compound is contacted with elemental bromine $Br_2$. The molar ratio of $Br_2$ to hydroxyaromatic compound is preferably less than 1:2, typically in the range of about 0.2–0.9:2, to minimize the conversion to dibromo and more highly brominated compound by-products.

The bromine may be added neat to the reaction vessel, or it may be added as a solution of bromine in a polar solvent. Examples include polar aprotic solvents such as acetonitrile, dimethyl sulfoxide, chloroform, ethyl acetate, and o-dichlorobenzene, as well as protic solvents such as water, acetic acid, propionic acid, and excess hydroxyaromatic compound. Acetic acid and acetonitrile are frequently preferred. Mixtures of the foregoing solvents may also be employed. When a solvent is used in the intial bromination (I) with $Br_2$, the same solvent is typically also used in the subsequent HBr bromination Reaction (II). However, each reaction is frequently run under anhydrous conditions.

As shown in Reaction (II), the HBr produced from Reaction (I) is used to brominate additional hydroxyaromatic compounds. This reaction is conducted by contacting the hydroxyaromatic compound with the HBr from (I) and oxygen in the presence of a metal catalyst. Furthermore, as previously mentioned, one or more polar organic solvents may also be present in the bromination reaction (II).

The molar ratio of HBr to hydroxyaromatic compound is preferably less than 1:1, again to minimize conversion to multi-brominated compounds; ratios in the range of about 0.2–0.9:1 are typical. As previously mentioned, the bromination reaction using HBr as the brominating agent may be conducted at a temperature ranging from about 20 to about 150° C., preferably about 60–80° C.

The oxygen is employed in stoichiometric excess and may be pure oxygen or may be employed in the form of air or oxygen-enriched air; ordinary air is often preferred. Contact may be made with flowing oxygen or air or under pressure, typically up to about 100 atm. The oxybromination reaction (II) occurs in the presence of a metal catalyst, such as elemental copper, a copper compound, or one or more compounds or complexes of Group IV–VIII transition metals of the Periodic Table of Elements, as described in copending, commonly owned U.S. patent application Ser. No. 10/650,567, filed Aug. 28, 2003, entitled "SELECTIVE CATALYTIC OXYBROMINATION OF HYDROXYAROMATIC COMPOUNDS".

When copper is used to catalyze the reaction, copper compounds are generally preferred. Examples are cupric sulfate, cupric chloride, cupric bromide, cuprous chloride and cuprous bromide. Of these, cupric bromide ($CuBr_2$) is often preferred by reason of its relatively low cost and particular suitability, as contact with hydrobromic acid will usually convert other cupric salts to the bromide. A molar ratio of hydroxyaromatic compound to the copper catalyst ranging from about 10:1 to about 200:1 is sufficient to catalyze the reaction. A ratio of 30:1 is typical.

When a compound/complex of a transition metal from Group IV–VIII of the Periodic Table of Elements is employed as the catalyst, suitable transition metals include vanadium, titanium, molybdenum, tungsten, and iron, for example. Vanadate salts, such as sodium metavanadate having the chemical formula $NaVO_3$, are preferentially used. Other suitable transition metal catalysts include, for example, bis(acetylacetonate)oxovanadium ($VO(acac)_2$), bis(acetylacetonate)oxotitanium ($TiO(acac)_2$), sodium molybdenum oxide dihydrate ($NaMoO_4 \cdot 2H_2O$), iron bromide ($FeBr_2$), and tungstic acid ($H_2WO_4 \cdot xH_2O$). Bis(acetylacetonate)oxovanadium has the chemical formula VO(CH$_3$COCHCOCH$_3$)$_2$, and bis(acetylacetonate)oxotitanium has formula TiO(CH$_3$COCHCOCH$_3$)$_2$. In addition, the Group IV–VIII transition metal catalyst compounds may be used alone or in combination, such as in a mixture. However, the invention is not limited to use of these transition metal catalysts, and other metals, ligands, and salts will be obvious to those of skill.

A molar ratio of hydroxyaromatic compound to the transition metal catalyst(s) ranging from about 1:1 to about 500:1 minimizes conversion of the products to dibromo and more highly brominated compounds. Typically, a molar ratio of 200:1 is employed.

The product of the each bromination reaction (I) and (II), and the combination (III), is usually predominantly the p-bromo compound, with minor amounts of o-bromo compound and dibromo and higher compounds also being present. The efficiency with respect to converting the initial charge of bromine to brominated products is usually greater than 70%, and often as high as 90%.

As used herein, "conversion" of phenol to bromophenols is defined as total phenol (in weight units or moles) consumed as a percentage of phenol originally present. Selectivity to 4-bromophenol is usually at least 60%, "selectivity" meaning moles of the specific product formed as a percentage of moles of phenol consumed. Furthermore, "monobromophenol selectivity" is defined herein as moles of para-brominated and ortho-brominated product formed as a percentage of moles of para-brominated products, ortho-brominated products, dibrominated products, and more highly brominated products formed. A monobromophenol selectivity of at least 76% is generally observed.

Separation of the bromophenol compounds prepared according to the invention may be effected by art recognized methods. Distillation is generally preferred, since there is a difference of more than 40° C between the boiling points of 2-bromophenol (194.5° C.) and 4-bromophenol (238° C.), and the dibromophenols have even higher boiling points. Distillation may be conducted under reduced pressure to minimize thermal decomposition.

The following examples are given by way of illustration and are not intended to be limitative of the present invention. The reagents, reactants, and catalysts used in the bromination reactions described herein are readily available materials.

Example 1 illustrates the bromination of phenol with Br$_2$ with no catalyst present, as depicted in Reaction (I), followed by the addition of CuBr$_2$ and running a subsequent reaction in the presence of air, as illustrated in Reaction (II). In this example, one molar equivalent of elemental bromine was added to at least two molar equivalents of the hydroxyaromatic compound, followed by addition of the metal catalyst and oxygen.

Example 2 illustrates the bromination of phenol with Br$_2$ in the presence of CuBr$_2$, without an excess of air pressure. Subsequently, the mixture was pressurized with air to consume the HBr produced in the first step. In Example 2, one molar equivalent of elemental bromine was added to at least two molar equivalents of the hydroxyaromatic compound in the presence of the metal catalyst, followed by the addition of oxygen.

Example 3 shows a system wherein all components except Br$_2$ are loaded into a pressurized reactor, and Br$_2$ is pumped in, as depicted above in Reaction (III). In this example, one molar equivalent of elemental bromine was added to at least two molar equivalents of the hydroxyaromatic compound in the presence of the metal catalyst and oxygen. Basically, this is a combination of the two steps described in Examples 1 and 2 into one reaction.

EXAMPLE 1

To a round bottom flask equipped with a magnetic stir bar and a reflux condenser was charged 55.4 g (0.58 moles) of phenol and 43.6 mL of water. Then an addition funnel containing 19.8 g (0.12 moles) of Br$_2$ was attached. Br$_2$ was added drop wise at room temperature with mixing. By GC analysis, 16% of the phenol was converted to a mixture of brominated phenolics. To this mixture, 3.57 g (0.02 moles) of CuBr$_2$ were added, and the resulting mixture was transferred to an autoclave reactor equipped with a mechanical stirring mechanism and subjected to 34.0 atm of air at 65° C. for one hour. Analysis of the resulting mixture by GC showed an additional 9% conversion of phenol to brominated phenolics. With respect to the initial mixture, 25% conversion of phenol was observed with 62% 4-bromophenol selectivity and 78% monobromophenol selectivity. The efficiency with respect to the initial charge of bromine was 72%.

EXAMPLE 2

To a round bottom flask equipped with a magnetic stir bar and a reflux condenser was charged 55.4 g (0.58 moles) of phenol, 3.57 g (0.02 moles) of CuBr2 and 43.6 mL of water. Then an addition funnel containing 19.8 g (0.12 moles) of Br$_2$ was attached. Br$_2$ was added drop wise at room temperature with mixing. The resulting mixture contained 1.44 wt. % 2-bromophenol, 8.17 wt. % 4-bromophenol and 6.67 wt. % 2,4-dibromophenol as determined by GC analysis of the mixture. The mixture was transferred to an autoclave reactor equipped with a mechanical stirring mechanism and subjected to 34.0 atm of air at 65° C. for one hour. Analysis of the resulting mixture by GC showed an additional 10% conversion of phenol to brominated phenolics. With respect to the initial mixture, 27% conversion of phenol was observed with 63% 4-bromophenol selectivity and 77% monobromophenol selectivity. The efficiency with respect to the initial charge of bromine was 75%.

EXAMPLE 3

To an autoclave reactor equipped with a mechanical stirrer and a glass liner was charged 55.4 g (0.58 moles) of phenol, 3.57 g (0.02 moles) of CuBr$_2$ and 43.6 mL of water. In a separate reservoir attached to an Eldex metering pump a solution containing 22.3 g of Br$_2$ in 82.5 g of acetic acid. The reactor was pressurized with 34.0 atm of air and heated to 65° C. The Br$_2$ containing solution was then pumped into the reactor at a rate corresponding to 0.09 g Br$_2$/min until 33.9 g (0.06 moles of Br$_2$) of the mixture was added. The reaction was allowed to proceed for 20 min. after addition of Br$_2$ was stopped. Analysis of the resulting mixture by GC showed 15% conversion of phenol with 63% 4-bromophenol selectivity and 76% monobromophenol selectivity. The efficiency with respect to the initial charge of bromine was 90%.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for preparing a brominated hydroxyaromatic compound which comprises contacting a hydroxyaromatic compound with oxygen and elemental bromine in the presence of a metal catalyst.

2. The method of claim 1, wherein one molar equivalent of said elemental bromine is added to at least two molar equivalents of said hydroxyaromatic compound, followed by addition of said metal catalyst and oxygen.

3. The method of claim 1, wherein one molar equivalent of said elemental bromine is added to at least two molar equivalents of said hydroxyaromatic compound in the presence of said metal catalyst, followed by addition of oxygen.

4. The method of claim 1, wherein one molar equivalent of said elemental bromine is added to at least two molar equivalents of said hydroxyaromatic compound in the presence of said metal catalyst and oxygen.

5. The method of claim 1, wherein said hydroxyaromatic compound has the formula

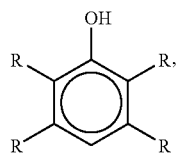

wherein each R is independently hydrogen or $C_{1-4}$ alkyl.

6. The method of claim 1, wherein said hydroxyaromatic compound is selected from the group consisting of phenol, o-cresol, and m-cresol.

7. The method of claim 6, wherein the hydroxyaromatic compound is phenol.

8. The method of claim 1, wherein said metal catalyst is selected from the group consisting of elemental copper, copper compounds, and one or more compounds or complexes of Group IV–VIII transition metals of the Periodic Table of Elements.

9. The method of claim 1, wherein said metal catalyst is a copper catalyst selected from the group consisting of cupric bromide, cupric sulfate, cupric chloride, cuprous chloride, or cuprous bromide.

10. The method of claim 9, wherein said metal catalyst is cupric bromide.

11. The method of claim 9, wherein a molar ratio of said hydroxyaromatic compound to said copper catalyst ranging from about 10:1 to about 200:1 is employed.

12. The method of claim 1, wherein said catalyst is selected from the group consisting of compounds of vanadium, titanium, molybdenum, tungsten, iron, and mixtures thereof.

13. The method of claim 12, wherein a molar ratio of said hydroxyaromatic compound to said catalyst ranging from about 1:1 to about 500:1 is employed.

14. The method of claim 1, wherein said catalyst is selected from the group consisting of sodium metavanadate, bis(acetylacetonate)oxovanadium, bis(acetylacetonate)oxotitanium, sodium molybdenum oxide dihydrate, iron bromide ($FeBr_2$), tungstic acid ($H_2WO_4 \cdot xH_2O$), and mixtures thereof.

15. The method of claim 1, wherein said contact is anhydrous.

16. The method of claim 1, wherein a polar solvent is also present.

17. The method of claim 16, wherein said solvent is selected from the group consisting of acetonitrile, dimethyl sulfoxide, chloroform, o-dichlorobenzene, water, phenol, o-cresol, m-cresol, propionic acid, and acetic acid.

18. The method of claim 16, wherein said solvent is acetonitrile or acetic acid.

19. The method of claim 1, wherein said oxygen is provided by air.

20. The method of claim 1, wherein flowing oxygen is employed.

21. The method of claim 1, wherein oxygen under pressure is employed.

22. The method of claim 1, wherein a temperature in the range of about 20–150° C. is employed.

23. The method of claim 1, wherein a molar ratio of said elemental bromine to said hydroxyaromatic compound less than 1:2 is employed.

24. A method for preparing 4-bromophenol, 4-bromo-2-methylphenol, or 4-bromo-3-methylphenol, which comprises contacting phenol, o-cresol, or m-cresol, respectively, with air and elemental bromine, in the presence of cupric bromide.

* * * * *